United States Patent [19]
Muller

[11] Patent Number: 4,950,246
[45] Date of Patent: Aug. 21, 1990

[54] INJECTION PEN

[75] Inventor: Robert H. Muller, Nieuwegein, Netherlands

[73] Assignee: Spruyt-Hillen B.V., Vianen, Netherlands

[21] Appl. No.: 187,015

[22] Filed: Apr. 27, 1988

[30] Foreign Application Priority Data

May 8, 1987 [NL] Netherlands ............... 87-01091

[51] Int. Cl.5 ............................................. A61M 5/20
[52] U.S. Cl. ................................. 604/154; 604/218; 128/DIG. 1
[58] Field of Search ................. 604/65, 67, 131, 151, 604/152, 154, 155, 187, 218; 128/DIG. 1, DIG. 12, DIG. 13; 222/326, 386; 73/239

[56] References Cited

U.S. PATENT DOCUMENTS

| | | | |
|---|---|---|---|
| 4,529,401 | 7/1985 | Leslie et al. | 128/DIG. 1 |
| 4,551,133 | 11/1985 | Zegers de Beyl et al. | 604/67 |
| 4,617,016 | 10/1986 | Blomber | 128/DIG. 1 |
| 4,627,835 | 12/1986 | Fenton, Jr. | 128/DIG. 1 |
| 4,634,431 | 1/1987 | Whitney et al. | 128/DIG. 1 |
| 4,685,903 | 8/1987 | Cable et al. | 604/151 |
| 4,741,732 | 5/1988 | Crankshaw et al. | 604/67 |

FOREIGN PATENT DOCUMENTS

85/02546 6/1985 PCT Int'l Appl. ............... 604/131

Primary Examiner—Stephen C. Pellegrino
Assistant Examiner—Ralph Lewis
Attorney, Agent, or Firm—Leonard Bloom

[57] ABSTRACT

An injection pen that is suitable for being carried in the clothes of a user-patient for the selective use thereof. The pen includes a housing having a cartridge having a variable content disposed therein. The cartridge has an outlet formed therein. A piston is disposed therein for altering the fluid content of the cartridge. A pump rod is biased against the piston for altering the fluid content of the cartridge. A drive mechanism is provided for moving the pump rod at a continuous rate. The electromotor is controlled by an electronic control unit including a memory means for storing data, such as that corresponding to the reservoir stock status and that corresponding to the number of units of injection fluid to be delivered to the user-patient. A comparator means is provided for comparing the number of units of fluid with the reservoir stock status for controlling the electromotor. Preferably, the control unit is an integrated circuit including a processor.

17 Claims, 2 Drawing Sheets

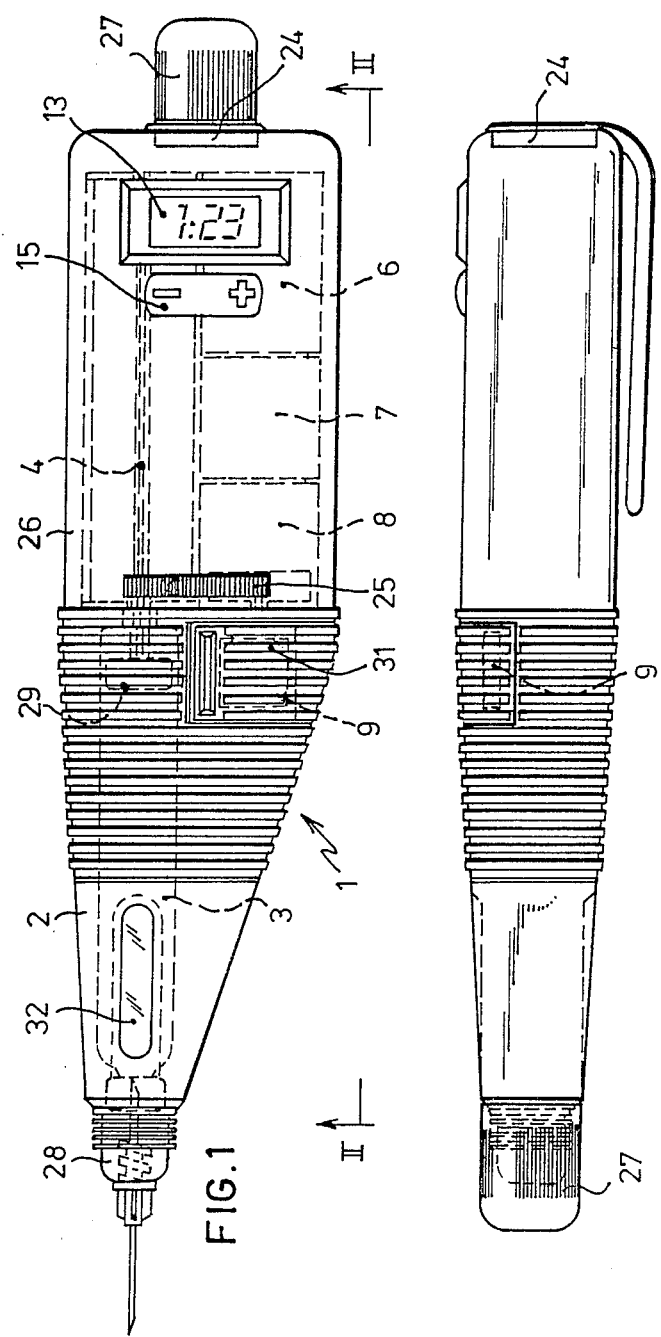

INJECTION PEN

The invention relates to an injection pen comprising a magazine for receiving an injection fluid reservoir or cartridge of a variable content, a pump rod to be biased against the reservoir for altering the content of the reservoir and a drive mechanism for moving the pump rod.

Such an injection pen is available on the market by the name of "NovoPen" and is supplied by Novo-Industri in Denmark. The pen was developed for administering insulin to diabetics, when on a so-called basal/prandial insulin regimen. In such a regimen the basal insulin requirement is met by one daily injection of time-released insulin. The postprandial requirement is met by preprandial injections of small quantities of short-term insulin. Thus the patient can vary the quantity of insulin to be administered and, in relation to that, also the quantity and moment of food intake. This freedom is further increased by the fact that the injection pen for the preprandial injections has such a size that it can easily be carried in garment pockets, such as an inside pocket of a jacket, and is therefore always within reach.

With this NovoPen a small dose (2 IE) can be administered by pressing a push button, causing a pump rod to move and displace, in its turn, a piston in a cartridge filled with insulin. When pressing the push button the user will hear two clicks. After the insulin has been delivered, the push button returns to its initial position, and the pump rod, as well as the piston, remain in place.

The invention aims to provide an injection pen of the type described in the introduction that comprises safeguards against injecting insulin in fatty tissue offering high counter-pressure. Furthermore an object is to construct the injection pen in such a manner that the patient can obtain visual information on e.g. the progress of the delivery of insulin. It is also an object of the invention that the pen should also be suited for use with non-prefilled insulin cartridges.

The injection pen according to the invention is, for the safe-guard against injecting insulin in fatty tissue, characterized in that the drive mechanism comprises an electromotor. With the electromotor the force exerted on the pump rod can be kept substantially constant at a desired level during driving. Even the exertion of too much (more than normally needed) force by the patient does not result in undesired delivery anymore.

The rotary movements of the electromotor can be converted through a gear and transmission system to a translation movement of the pump rod. This also shifts the piston, thus displacing the insulin fluid.

The control of the drive mechanism is preferably realized with the aid of an electronic control unit, also integrated in the injection pen. The power required for driving and controlling can be supplied by a battery incorporated in the pen.

A number of functions that are not available in the known injection pen and that have to be performed by the user himself can be included in the injection pen with the electronic control unit. By having the control unit comprise at least one integrated circuit comprising a processor, its size can be kept limited and the injection pen will maintain its pen-like appearance, so that it can be easily carried by a patient.

In view of the items stated in the preceding paragraph the control unit can comprise memory means, part of which has preferably been assigned as first dose memory means for storing a data corresponding with a certain number of dose units of injection fluid.

In order to enable the patient to visually obtain information on e.g. the progress of the insulin delivery the injection pin according to the invention comprises a display controlled at least by the first dose memory means. The display shows the user said certain number of dose units stored as a data in the first dose memory means. For the sake of a visually handicapped user the pen can comprise, apart from the display, a tone signal generator controlled by at least the first dose memory means.

In order to set the dose that is to be injected the pen can comprise a dose set unit that is externally operable, as well as an up/down counter circuit means integrated in the control unit that alters the data stored in the first dose memory means in response to signals outputted by the dose set unit up to a data corresponding with the desired dose set value.

By the dose set unit to be operated by the patient the data stored in the first dose memory means can be set by means of the up/down counter circuit means to a set value that corresponds with the desired dose. The set value is displayed on the display in the form of dose units or emitted in the form of tone signals from the tone signal generator.

According to a preferred embodiment the injection pen is equipped with a measuring unit for measuring the stock in the reservoir. The measuring unit preferably comprises a sensor for determining the position of the pump rod. Furthermore the control unit can comprise a down counter circuit means that is controlled by the data from the measuring unit and that decreases the data that is stored in the first dose memory means accordingly. Thus each delivered insulin unit is registered and, through connection with the first dose memory means, shown on the display and, if available, emitted by the tone signal generator.

Furthermore in the memory means areas can have been assigned as reservoir stock memory means. The control unit preferably comprises an up/down counter circuit means that is controlled by the data from the measuring unit and that alters the data stored in the reservoir stock memory means accordingly. Thus in the same manner as with the first dose memory means the data stored in the reservoir stock memory means is adapted to the actual situation.

The control unit can comprise comparator means that receive signals from the first dose memory means and the reservoir stock memory means and control the operation of the electromotor. With the aid of the comparator means the set value of the desired dose of insulin is compared with the available insulin stock. If the set value exceeds the available stock the action of the electromotor is blocked by the comparator means, so that no insulin can be delivered. According to a preferred embodiment of the injection pen the display and/or the tone signal generator is co-controlled by the comparator means. Thus the patient's notice can be drawn to the fact that the insulin stock is not sufficient for the quantity to be delivered, desired by him.

According to a preferred embodiment of the injection pen according to the invention the control unit comprises timing means, which receive a signal corresponding to the stock status and, in response thereto, control the operation of the electromotor. This provision is closely related to the fact that the electromotor maintains the pressure with which the pump rod is biased against the piston at a certain level. By using the timing means the electromotor can be made to stop after a determined period of time has lapsed in which, contrary to what was intended, no insulin delivery could take place since the counterpressue exceeded the pump pressure. This being stopped of the electromotor is an extra safeguard against injecting insulin in undesired places such as in fatty tissue.

According to another preferred embodiment of the injection pen according to the invention the memory means have areas assigned as second dose memory means for storing a data corresponding with the dose set value, which second dose memory means are fed direct by the battery. With the aid of the second dose memory means, which also keep the data stored in them after the injection pen has been switched off, information can be obtained on the size of the previous insulin delivery upon switcing the injection pen on again.

The electromotor can be of reversible construction so that the injection pen according to the invention is also suitable for use with non-prefilled insulin cartridges. As a result the pump rod can also be moved in the opposite direction. Then the piston is moved along in the reservoir and insulin can be drawn in as a consequence of the thus created under-pressure. This has the advantage that the injection pen can also be used without prefilled cartridges.

The means indicated above as such have preferably been included in the integrated circuit. In this way the control unit can remain small, so that the size of the injection pen according to the invention can be kept limited, in spite of the great number of functions it incorporates. Thus the injection pen according to the invention is very handy and user-friendly.

The injection pen according to the invention will hereafter be described on the basis of the drawing, in which:

FIG. 1 schematically represents the structure of the injection pen;

FIG. 2 represents a view along the arrows II—II in FIG. 1, with displaced cap, however;

Figure 3:
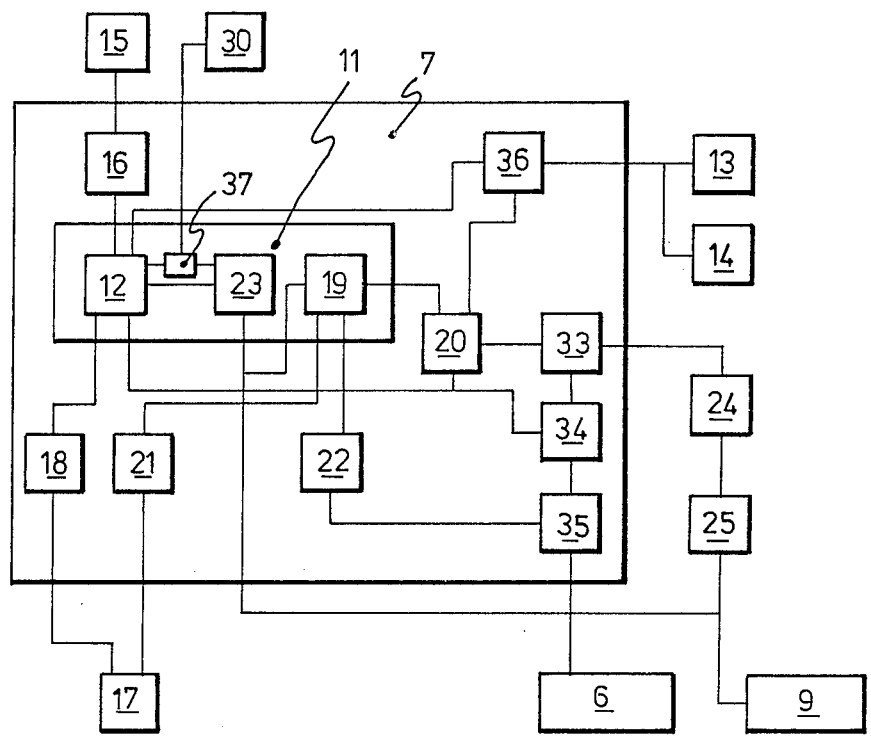
FIG. 3 represents a block diagram of i.a. the electronic control unit of the injection pen.

The housing 26 of the injection pen 1 represented in FIG. 1 incorporates i.a. a magazine 2 in which an insulin reservoir 3 can be disposed, a pump rod 4 and, as drive mechanism for the pump rod, an electromotor 6, that can be a DC motor. The insulin reservoir 3 can e.g. be a cartridge of the trademark Actrapid HM Penfill commercially available.

The injection pen 1 is shown in FIG. 1 in its ready-to-use condition. A needle unit 28, comprising a needle and a needle retainer, is screwed onto the head after the cap 27 is displaced from the head to the starter unit 24 of pen 1. When applying the needle unit 28 the needle tip situated within the pen 1 is pushed through a rubber membrane of the reservoir into flowing contact with the insulin contained therein. At the other end of the reservoir 3 there is a piston 29 that can be displaced inside the reservoir for forcing out insulin through the needle into the patient's connective tissue. The displacement of the piston 29 is effected by the translation of the pump rod 4, which movement is caused by the rotary movements of the electro motor 6 converted by a gear/transmission system 8.

FIG. 1 also shows a battery 9 for feeding the electromotor 6 and an electronic control unit 7, which will be further elucidated later in this description. Battery 9 can be reached for replacement through a panel 31. A main switch 25 serves to switch the injection pen on or off. Furthermore FIG. 1 shows a sight-glass 32, possibly disposed on either side of the injection pen 1. This can be used to obtain information on the stock status in reservoir 3. This information is an extra feature beside the electronically controlled information.

The injection pen represented in FIG. 1 has, in spite of the presence of an electromotor and electronic control unit, such dimensions that it can easily be carried by a patient, e.g. in the inside pocket of his jacket. This makes it easier for a patient to pursue an insulin regimen. The injection pen 1 has e.g. a length of 14 cm, a width of 2 cm and a height of 3 cm.

The flat shape of the pen 1 can be clearly perceived in FIG. 2. Also visible is a clip with which the pen can e.g. be clipped to the inside pocket of a jacket.

The block diagram in FIG. 3 shows the schematic structure of the electronic control unit with a few provisions connected thereto, all in accordance with a preferred embodiment of the injection pen 1. In the control unit, comprising at least one integrated circuit incorporating a processor, a memory 11, including a first dose memory 12, a second dose memory 23 and a reservoir stock memory 19, an up/down counter circuit 16 for the first dose memory 12, a down counter circuit 18 also for the first dose memory 12, an up/down counter circuit 21 for the reservoir stock memory 19 and a timer 22 are all incorporated. Furthermore it comprises some gate circuits 33, 34, 35, 36, 37. A display 13 and/or tone signal generator 14, a sensor 17, a dose set unit 15 and the electromotor 6 are all connected to the electronic control unit 7. Furthermore FIG. 3 shows the battery 9, the main switch 25, the starter unit 24 and the push button 30.

The mutual relations of the means in the control unit 7 and their relations to provisions disposed outside the control unit will be further elucidated hereafter by means of a full operating cycle.

The injection pen 1 is switched on by operating the main switch 25. The display 13 shows a zero. By pushing the push button 30 the data stored in the second dose memory 23 is also stored, via AND-gate circuit 37, in the first dose memory 12, in its turn, optionally via Exclusive OR-gate circuit 36, represented as number of dose units on display 13. This number of dose units equals the number of dose units delivered during the previous injection. Since the second dose memory 23 is fed direct by battery 9 this data is retained, irrespective of the position of the main switch 25.

If the patient wishes to alter the number of dose units shown on display 13, he can do so by pushing the plus or minus button of the dose set unit 15. Via the up-/down counter circuit 16 the data in the first dose memory 12 is then adjusted and so is the number of dose units shown on display 13, in accordance with the patient's wishes. Instead of or beside the display 13 a tone signal generator 14 can be provided, with which a visually handicapped user can obtain similar information by means of tone signals of different pitch (corresponding to a certain number of dose units) and by short tone signals at each change of the set number of dose units.

After the desired number of dose units has been set and the dose set unit 15 has been delivered, the set value is compared, with the aid of the comparator 20, with the insulin stock in the reservoir, stored as a data in the reservoir stock memory 19. When the number of set dose units exceeds the number of insulin units in the reservoir, the comparator 20 renders the operation of the starter unit 24 ineffective, and it causes the display 13 to lighten up and/or the tone signal generator to emit a certain tone signal. For that purpose the comparator 20 can be connected with the first dose memory 12 via Exclusive OR-gate circuit 36 to the display 13 and/or tone signal generator 14. By operating the minus button of the dose set unit 15 the set dose, stored in the first dose memory 12 and shown on display 13 and/or made heard by the tone signal generator 14, is reduced by one unit at the time. The display 13 continues to light up and/or the tone signal generator 14 continues to emit said tone signal until the set number of dose units corresponds with the number of insulin units contained in the reservoir 3. This number is stored as a data in the second dose memory 23. When the set number of dose units is smaller than or equal to the number of insulin units contained in the reservoir then the set number, stored as a data in the first dose memory 12, is also stored as a data in the second dose memory 23.

Subsequently an aseptically packed needle unit can be screwed in the head of the injection pen 1, the one end situated within the pen 1 penetrating into the reservoir 3. Then the patient can place the injection pen 1 on the desired spot on the body and the delivery of the set insulin dose can be started by pushing the cap 27 placed on the starter unit 24. The electromotor 6 is fed by battery 9 as long as the cap is pressed downwards and moves the pump rod 4 forward so that the piston 29 in the reservoir 3 forces insulin through the needle towards the patient's body.

Starter unit 24, comparator 20, and the first dose memory 12 can be connected to the electromotor 6 through AND-gate circuits 33 and 34.

With the aid of a sensor 17 the progress of the pump rod 4 at the delivery of each insulin unit is observed. In response to the data of the sensor 17 the data stored in the first dose memory 12 is adapted by down counter circuit 18 and the data stored in the reservoir stock memory 19 by an up/down counter circuit 21 at each delivered insulin unit. When the data stored in the first dose memory 12 changes, the number of insulin units that is still to be delivered, shown on display 13 or made audible by tone signal generator 14, changes as well. This way the patient can follow the progress of the delivery.

When the data stored in the first dose memory 12 equals zero units, i.e. when the set dose has been delivered, by means of the presence of the gate circuits 34 the interruption of the supply from the battery to the electromotor is effected. Since the reservoir stock memory 19 and the second dose memory 23 are fed direct by the battery the data stored therein is retained after operating the main switch 25.

When the patient inserts the needle of the injection pen, the situation may very well occur that the needle is inserted not far enough, viz. that it is inserted in fatty tissue. The counterpressure on account of the high mesh rate of the tissue is higher than the pressure in the deep, subcutane connective tissue with a low mesh rate. Under those circumstances, with the injection pen according to the invention undesired delivery of insulin is prevented, since the forward motion of the piston in the reservoir is not effected by the manual force of the patient but by the force supplied by the electromotor 6. The force that can be exerted on the piston 29 by this electromotor is limited to e.g. about 10N, sufficient to enable delivery into connective tissue and insufficient for (undesired) delivery in the wrong place, e.g. in fatty tissue. To prevent the electromotor from running on in spite of the fact that insulin delivery cannot take place a timer 22 has been incorporated in the control unit 7. This timer 22 can e.g. receive a signal from the reservoir stock memory 19 which corresponds with the data stored therein and if this data in the reservoir stock memory 19 has not changed over a certain period, e.g. 1 second, which implies that no delivery takes place, it can stop the electromotor 6 through the AND-gate circuit 35. The electromotor is also safe-guarded against running wild.

The electromotor 6 can be constructed reversible, so that the pump rod, and thus the piston, can be moved in the opposite direction. If the patient does not have insulin-filled cartridges at his disposal, with the aid of this provision an empty reservoir 3, disposed in the injection pen 1, can be filled with insulin by inserting the needle in an external quantity of insulin and, subsequently, retracting the piston 29 in the reservoir 3 with the aid of electromotor 6. By means of the presence of sensor 17 and up/down counter circuit 21 the data in the reservoir stock memory 19 is brought into agreement with the filling rate of the reservoir 3. This is also the case when an empty reservoir is not refilled but replaced by a prefilled insulin reservoir, if available.

In order to have the injection pen perform all the above functions and yet remain at an easy-to-handle size, the injection pen 1 according to the preferred embodiment the above means of the control unit 7, the memory 11, the circuits 16, 18, 21, comparator 20 and timer 22 have been incorporated in an integrated circuit. Gate circuits 33, 34, 35, 36 and 37 could also be incorporated in this integrated circuit. Thus an injection pen is obtained that is extremely user-friendly since, apart from its handy design, it can also perform a considerable number of functions that facilitate the use of said injection pen.

I claim:

1. In an injection pen suitable for being carried in the clothes of a user-patient and for being connected to the patient only during distinct one at a time injections, the injection pen being of the type including an elongated housing having a handle means around the outside adapted to be gripped within the fingers of the user-patient, the housing incorporating a magazine for an injection fluid cartridge having a variable fluid volume, the cartridge further having an outlet formed therein and a piston disposed therein, the pen having a pump rod that can be biased against the piston disposed in said cartridge for altering the fluid volume thereof, a head portion at one end of the elongated housing adapted to receive a needle unit for transferring fluid expelled from the cartridge through the outlet thereof to the body of the user-patient, and a drive mechanism for moving said pump rod and the piston, wherein the improvement thereupon comprising, in combination, the drive mechanism including an electromotor which is controlled by an electronic control unit comprising memory means, said memory means having areas assigned as first dose memory means, for storing a data corresponding to a certain number of dose units of injection fluid, the pen further incorporating an externally operable dose set unit for setting said data, an indicator means controlled by said first dose memory means for representation of said certain number to the user-patient and a power source connected to the drive mechanism, the electronic control unit, the dose set unit and the indicator means for providing power thereto.

2. Injection pen according to claim 1, wherein the improvement thereupon, in combination, further comprises a measuring unit for measuing the stock in the cartridge, said control unit comprising a down counter circuit means that is controlled by the data from said measuring unit and reduces the data stored in said first dose memory means accordingly.

3. Injection pen according to claim 2, wherein the improvement thereupon, in combination, further comprises said memory means having areas assigned as reservoir stock memory means for storing a data corresponding to the number of units of injection fluid present in the cartridge, said reservoir stock memory means being directly fed by the power source and in that said control unit comprises an up/down counter circuit means that is controlled by the data from said measuring unit and alters the data stored in said reservoir stock memory means accordingly.

4. Injection pen according to claim 3, wherein the improvement thereupon, in combination, further comprises said control unit including comparator means that receive signals from said first does memory means and said reservoir stock memory means, said comparator means controlling the operation of said electromotor and the indicator means.

5. Injection pen according to claim 4, wherein the improvement thereupon, in combination, further comprises said comparator means being incorporated in an integrated circuit incorporating a processor and being comprised in said control unit.

6. Injection pen according to claim 3, wherein the improvement thereupon, in combination, further comprises said up/down counter circuit means being incorporated in an integrated circuit incorporating a processor and being comprised in said control unit.

7. Injection pen according to claim 2, wherein the improvement thereupon, in combination, further comprises said measuring unit having a sensor for determining the position of said pump rod.

8. Injection pen according to claim 2, wherein the improvement thereupon, in combination, further comprises said down counter circuit means being incorporated in an integrated circuit incorporating a processor and being comprised in said control unit.

9. Injection pen according to claim 1, wherein the improvement thereupon, in combination, further comprises said control unit having timing means which receive a signal corresponding to the stock status in the cartridge and in response thereto control the operation of said electromotor.

10. Injection pen according to claim 9, wherein the improvement thereupon, in combination, further comprises said timing means being incorporated in an integrated circuit incorporating a processor and being comprised in said control unit.

11. Injection pen according to claim 1, wherein the improvement thereupon, in combination, further comprises said memory means having areas assigned as second dose memory means for storing a data corresponding with the data stored in said first dose memory means, said second dose memory means being directly fed by the power source.

12. Injection pen according to claim 1, wherein the improvement thereupon, in combination, further comprises said memory means being incorporated in an integrated circuit incorporating a processor and being comprised in said control unit.

13. Injection pen according to claim 1, wherein the improvement thereupon, in combination, further comprises said piston being attachable to the pump rod and the electromotor is reversible for retracting said pump rod, and thereby refilling said cartridge with injection fluid.

14. In an injection pen for the delivery of fluid to a user-patient in need thereof, the pen being of the type that is attached to the user-patient only during distinct one at a time injection use thereof, and that is suitable for being carried in the clothing of the user-patient, the improvement thereupon, in combination, comprising:

an elongated housing having a handle means around the outside adapted to be gripped within the fingers of the user-patient, the housing incorporating a magazine for an injection fluid cartridge;

the injection fluid cartridge having a variable fluid volume, the cartridge further having a fluid outlet formed therein and a piston disposed in the cartridge;

a pump rod biased against the piston disposed in said cartridge for altering the fluid volume thereof;

a head portion at one end of the elongated housing adapted to receive a needle unit for receiving fluid expelled from the cartridge through the outlet thereof and for transferring said expelled fluid to the user-patient in need thereof;

a drive mechanism for moving said pump rod and the piston, said drive mechanism comprising an electromotor which is controlled by an electronic control unit including at least one integrated circuit incorporating a processor, and a battery;

said control unit comprising memory means incorporated in said integrated circuit, said memory means having areas assigned as first dose memory means for storing a data corresponding to a certain number of dose units of injection fluid, as second dose memory means for storing a data corresponding with the data stored in said first dose memory means and being fed direct by said battery, and as reservoir stock memory means for storing a data corresponding to the number of units of injection fluid present in said cartridge and being fed direct by said battery;

an externally operable dose set unit for setting the data stored in said first dose memory means;

an indicator means controlled by said first dose memory means for making known said certain number of dose units to the user-patient;

a measuring unit for measuring the stock in the cartridge, said measuring unit comprising a sensor for determining the position of said pump rod;

the control unit being incorporated in the integrated circuit;

a down counter circuit means that is controlled by the data from said measuring unit and reduces the data stored in said first dose memory means accordingly;

an up/down counter circuit means that is controlled by the data from said measuring unit and alters the data stored in said reservoir stock memory means accordingly; and comparator means that receive signals from said first dose memory means and said reservoir stock memory means, said comparator means controlling the operation of said electromotor and the indicator means.

15. Injection pen according to claim 14, wherein the improvement thereupon, in combination, further comprises said control unit including timing means which receive a signal corresponding to the stock status in the cartridge and in response thereto control the operation of said electromotor.

16. Injection pen according to claim 15, wherein the improvement thereupon, in combination, further comprises said timing means being incorporated in said integrated circuit incorporating a processor and being comprised in said control unit.

17. Injection pen according to claim 14, wherein the improvement thereupon, in combination, further comprises said piston being attachable to the pump rod and the electromotor is reversible for retreating said pump rod, and thereby refilling said cartridge with injection fluid.

* * * * *